United States Patent [19]
Stobie et al.

[11] Patent Number: 5,755,783
[45] Date of Patent: May 26, 1998

[54] SUTURE RINGS FOR ROTATABLE ARTIFICIAL HEART VALVES

[76] Inventors: Robert Stobie, 27502 Los Banos, Mission Viejo, Calif. 92691; George Guo, 34 Club Vista, Dove Canyon, Calif. 92679

[21] Appl. No.: 688,672

[22] Filed: Jul. 29, 1996

[51] Int. Cl.$^6$ ................................................ A61F 2/24
[52] U.S. Cl. ................................................ 623/2; 623/900
[58] Field of Search ................................ 623/2, 900

[56] References Cited

U.S. PATENT DOCUMENTS

| | | |
|---|---|---|
| 4,197,593 | 4/1980 | Kaster et al. |
| 4,345,340 | 8/1982 | Rosen. |
| 4,535,483 | 8/1985 | Klawitter et al. ............ 623/2 |
| 4,680,031 | 7/1987 | Alonso ...................... 623/2 |
| 4,816,029 | 3/1989 | Penny, III et al. ............ 623/2 |
| 4,863,460 | 9/1989 | Mogladry .................. 623/900 |
| 4,892,540 | 1/1990 | Vallana ...................... 623/2 |
| 5,035,709 | 7/1991 | Wieting et al. |
| 5,071,431 | 12/1991 | Sauter et al. ............... 623/2 |
| 5,104,406 | 4/1992 | Curcio et al. ............. 623/900 |
| 5,147,391 | 9/1992 | Lane ........................ 623/2 |
| 5,178,633 | 1/1993 | Peters ....................... 623/2 |
| 5,258,023 | 11/1993 | Reger ........................ 623/2 |
| 5,354,330 | 10/1994 | Hanson et al. |
| 5,397,346 | 3/1995 | Walker et al. ............... 623/2 |
| 5,397,348 | 4/1995 | Campbell et al. ............. 623/2 |
| 5,480,425 | 1/1996 | Ogilive ...................... 623/2 |
| 5,487,760 | 1/1996 | Villafana ................... 623/2 |
| 5,607,470 | 3/1997 | Milo ......................... 623/2 |

FOREIGN PATENT DOCUMENTS

| | | |
|---|---|---|
| 70259 | 6/1952 | European Pat. Off. |
| 75530 | 9/1982 | European Pat. Off. |
| 119357 | 12/1983 | European Pat. Off. |
| 200926 | 4/1986 | European Pat. Off. |
| 350302 | 7/1989 | European Pat. Off. |
| 541215 | 8/1992 | European Pat. Off. |
| WO 82/02829 | 9/1982 | WIPO. |
| WO 92/19184 | 11/1992 | WIPO. |
| WO 93/20781 | 10/1993 | WIPO. |
| WO 94/01060 | 1/1994 | WIPO. |
| WO 95/16408 | 6/1995 | WIPO. |
| WO 95/28899 | 11/1995 | WIPO. |

OTHER PUBLICATIONS

International Search Report dated Nov. 6, 1997.

*Primary Examiner*—Paul B. Prebilic
*Attorney, Agent, or Firm*—Debra D. Condino; Guy L. Cumberbatch

[57] ABSTRACT

A suture ring for a rotatable artificial heart valve apparatus has a ring member covered by a fabric material. A portion of the fabric material covers a portion of the inner surface of the ring member. At least one protuberance is formed on the inner surface of the ring member so as to mitigate the frictional resistance to rotation which results from compression of the fabric between the suture ring and the heart valve. Thus, desirable rotation of the heart valve relative to the suture ring is assured over a range of thicknesses of the fabric material.

40 Claims, 5 Drawing Sheets

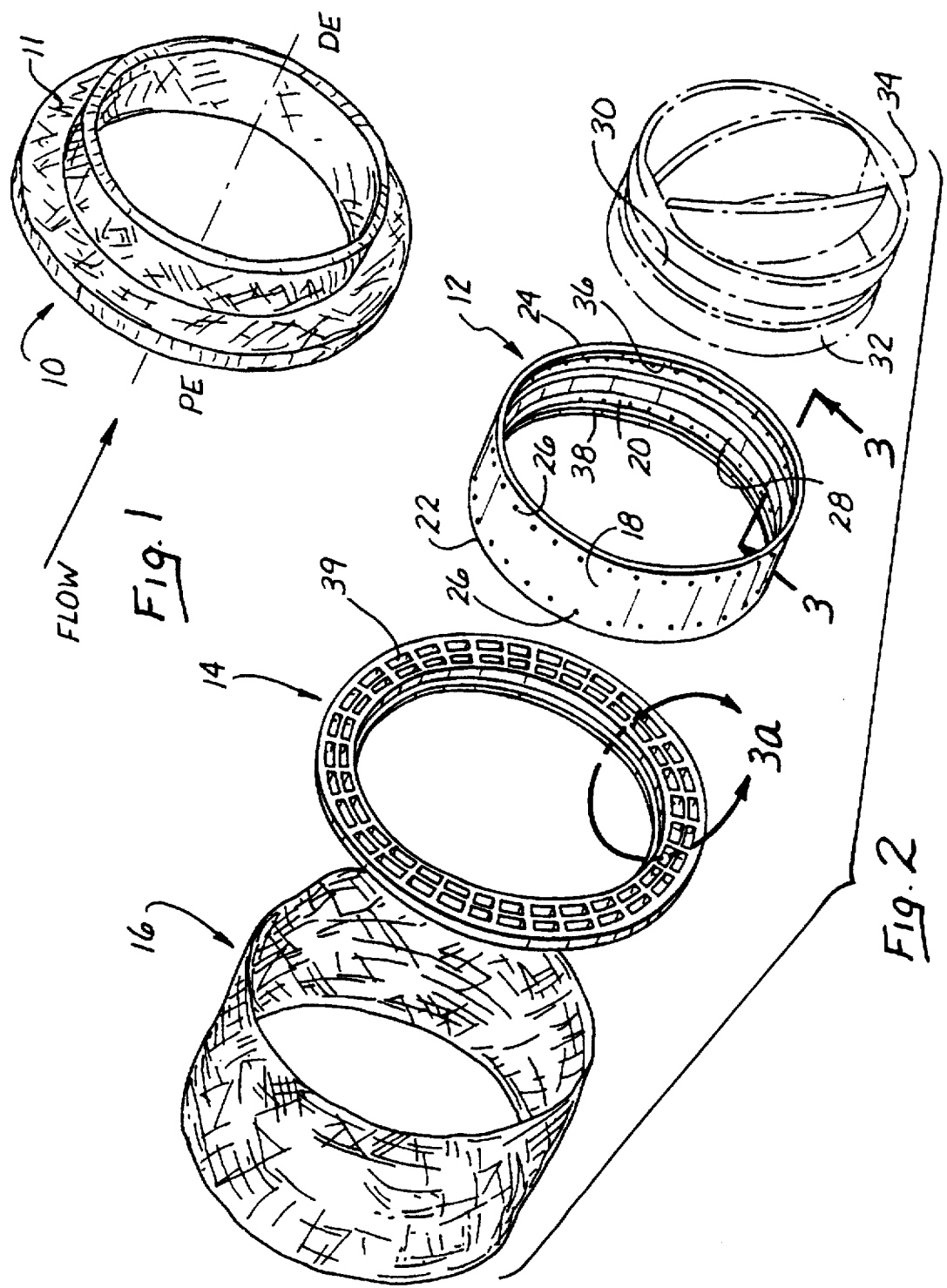

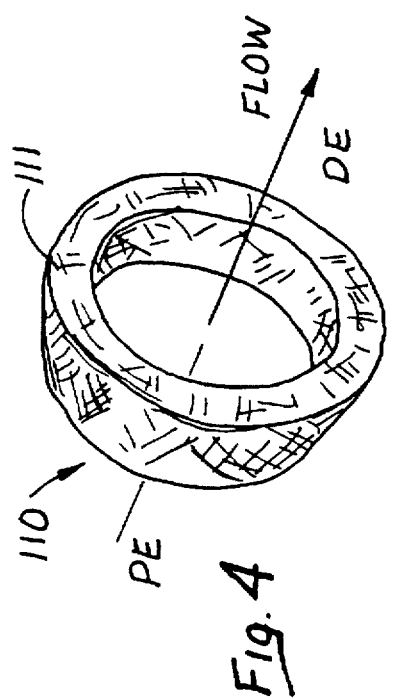
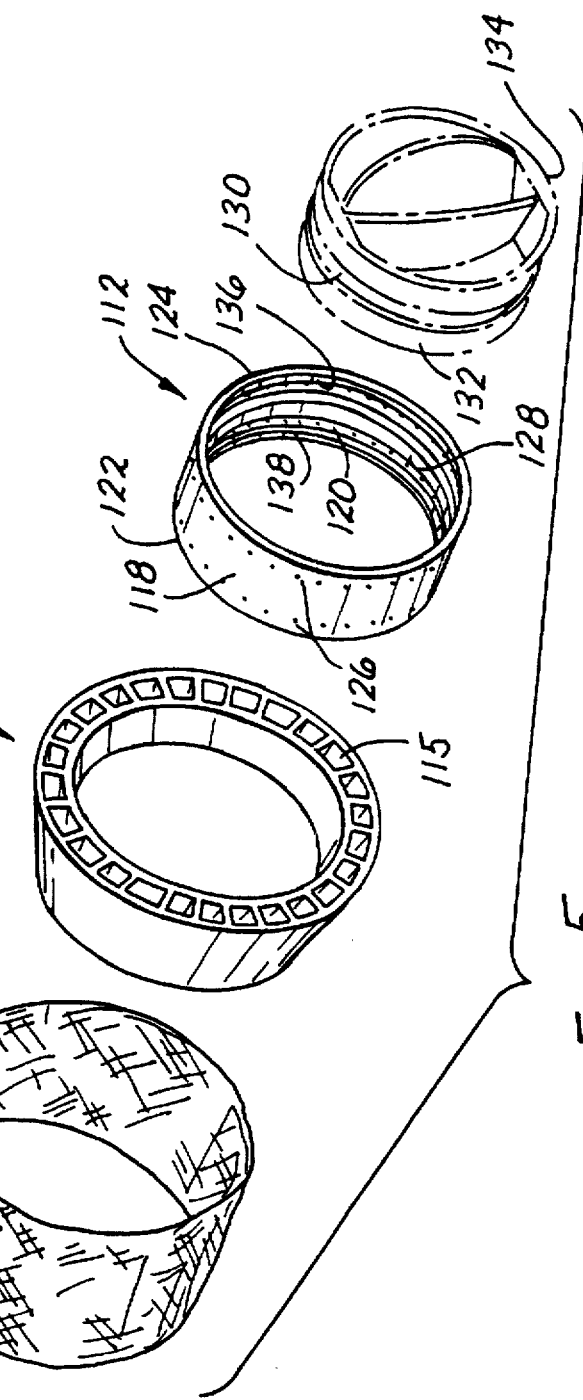

SUTURE RINGS FOR ROTATABLE ARTIFICIAL HEART VALVES

FIELD OF THE INVENTION

The present invention relates generally to medical devices and more particularly to heart valve prostheses having improved suture rings which facilitate consistent rotatability of the heart valve body within the suture ring.

BACKGROUND OF THE INVENTION

The prior art has included many prosthetic mechanical heart valves which may be surgically implanted to replace malfunctioning or diseased endogenous anatomical heart valves.

Among the prosthetic mechanical heart valves of the prior art are included a number of "rotatable" valves. These rotatable valves typically comprise an annular valve body having one or more occluder leaflets pivotally mounted within the annular valve body such that the leaflet(s) will open and close in response to hemodynamic forces of the blood. In this regard, the leaflets move back and forth between an open position whereby blood is permitted to outflow through the annular valve body, and a closed position whereby blood is prevented from backflowing through the annular valve body. A needle-penetrable suture ring is mounted about the outer surface of the annular valve body, and is sutured directly to the endogenous valve annulus of the patient-host. After the suture ring has been firmly sutured to the host tissue, the surgeon may manually rotate the valve body to place the occluder leaflets of the valve in their desired orientation prior to completion of the surgical procedure. Thus, it is necessary for the annular valve body to remain freely rotatable within the suture ring, to facilitate such manual rotation of the valve body by the surgeon. If the annular valve body does not freely rotate within the suture ring, it may be necessary for the surgeon to apply excessive pressure or torque to effect the desired rotation of the annular valve body. The application of excessive pressure or torque to the annular valve body carries a risk of: a) damaging the valve; or b) tearing the sutures which hold the suture ring of the annular valve body in affixation to the host tissue.

In view of the risks associated with the application of excessive pressure or torque to the annular valve body, it is desirable for rotatable prosthetic heart valves to be designed such that the amount of pressure or torque required to effect rotation of the annular valve body within the suture ring is consistently within acceptable limits, thereby avoiding any need for the application of excessive pressure or torque during the surgical procedure.

One example of a rotatable prosthetic heart valve of the prior art is described in U.S. Pat. No. 4,892,540 (Villana) and is manufactured and sold in at least some countries of the world as the Sorin Bicarbon™ Valve, by Sorin Biomedica S.p.A., Saluggia, Italy. The rotatable prosthetic heart valve of U.S. Pat. No. 4,892,540 (Villana) comprises an annular valve body having a pair of leaflets pivotally mounted therewithin, and an annular suture ring rotatably mounted therearound. An annular suture ring tracking groove is formed in the outer surface of the annular valve body. The suture ring is formed of a rigid inner ring member having an annular tracking rib formed on the inner surface thereof, and a woven or knitted fabric cover. The annular tracking rib of the rigid suture ring member is snap-fit into the annular tracking groove formed in the outer surface of the valve body. In this manner, the engagement of the tracking rib within the tracking groove serves to hold the suture ring in substantially fixed longitudinal position on the valve body, while allowing the suture ring to remain rotatable relative to the valve body. The fabric cover of the suture ring extends partially between the outer surface of the annular valve body, and the adjacent rigid suture ring member. In this regard, a portion of the fabric material is interposed or captured between the outer surface of the annular valve body and the adjacent inner surface of the rigid ring member. As a result, variations in the thickness of the fabric material used in the manufacture of the suture ring may result in variations in the amount of pressure or torque required to effect rotation of the annular valve body within the suture ring. For example, if the fabric used in the manufacture of the suture ring is relatively thin, very little frictional drag will result from the interposition of the fabric between the outer surface of the annular valve body and the inner surface of the rigid suture ring member, thereby allowing the annular valve body to be rotated with minimal force or torque. On the other hand, if the fabric material used in the manufacture of the suture ring is relatively thick, a greater amount of frictional drag will result from the interposition of the fabric material between the outer surface of the annular valve body and the inner surface of rigid suture ring member, thereby causing excessive force or torque to be required to effect rotation of the annular valve body within the suture ring.

In view of the above-explained potential for variations in fabric thickness in the suture rings to result in corresponding variations in the amount of force or torque required to effect rotation of the annular valve body, it is desirable to design alternative constructions for the annular valve body and/or suture ring to minimize the effect of variations in fabric thickness on the amount of pressure or torque required to effect rotation of the valve within the suture ring.

SUMMARY OF THE INVENTION

The present invention comprises an improvement in the mode of construction and design of rotatable prosthetic heart valves so as to minimize or prevent untoward variations in the force required to rotate the valve within the suture ring, irrespective of normal variations in the thickness of the fabric which covers the suture ring and which is at least partially interposed between the outer surface of the annular valve body and the rigid inner frame or ring member of the suture ring mounted thereon. Broadly stated, the improvement of the present invention comprises the formation of one or more protuberances on the rigid suture ring member and/or the annular valve body to mitigate the surface area between which the fabric material will be pinched or captured.

In accordance with the present invention, there is provided a suture ring which is rotatably mountable on a prosthetic heart valve of the type comprising an annular valve body having one or more occluder leaflets mounted therewithin, and wherein the annular valve body has an outer surface whereupon the rotatable suture ring is mountable. At least one protuberance (e.g., an annular rib) is formed on either the inner surface of the rigid suture ring member or the outer surface of the annular valve body, adjacent the region (s) wherebetween the fabric material will be pinched or captured. The formation of such protuberance(s) on either the outer surface of the annular heart valve body or the inner surface of the rigid suture ring member serves to decrease the total surface area of these components between which the fabric material will be pinched or captured. In this regard, the provision of such protuberance(s) will lessen the amount of frictional resistance to suture ring rotation which will occur as the thickness of the fabric material increases.

Further in accordance with the invention, there is provided a rotatable heart valve of the foregoing character, comprising an annular valve body having at least one occluder leaflet pivotally mounted therewithin, and a rotatable suture ring of the present invention rotatably mounted on the outer surface thereof. The fabric covering of the suture ring is at least partially interposed between the outer surface of the annular valve body and the inner surface of the rigid suture ring member, such that the fabric-contacting surface area is no more than 20% of the total surface which would otherwise be in direct contact with, and creating friction with, the fabric if the friction-mitigating protuberances were not present.

Further objects and advantages of the present invention will become apparent to those skilled in the art upon reading and understanding the following detailed description of a presently preferred embodiment of the invention.

BRIEF DESCRIPTION OF THE DRAWINGS

FIG. 1 is a distal perspective view of a suture ring for a rotatable artificial mitral valve according to the present invention;

FIG. 2 is an exploded distal perspective view of the suture ring of FIG. 1, additionally showing the mitral valve in phantom;

FIG. 4 is a distal perspective view of a suture ring for a rotatable artificial aortic valve according to the present invention;

FIG. 5 is an exploded distal perspective view of the suture ring of FIG. 4, additionally showing the aortic valve in phantom;

DETAILED DESCRIPTION OF THE PREFERRED EMBODIMENT

Figure 3:
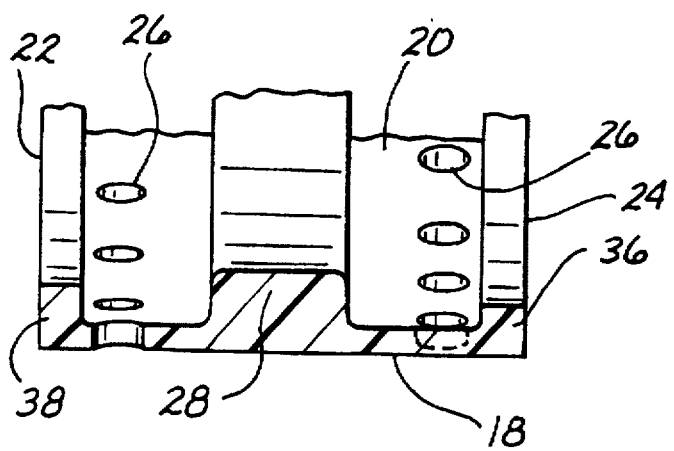
FIG. 3 is an enlarged cross sectional view of the ring member of the suture ring of FIG. 2, taken along line 3 thereof.
Figure 3A:
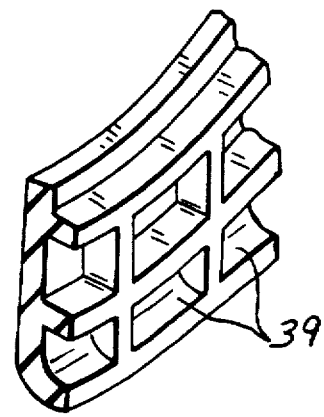
FIG. 3a is an enlarged fragmentary perspective view of the annular sponge of FIG. 2, taken within line 3a thereof.
Figure 8:
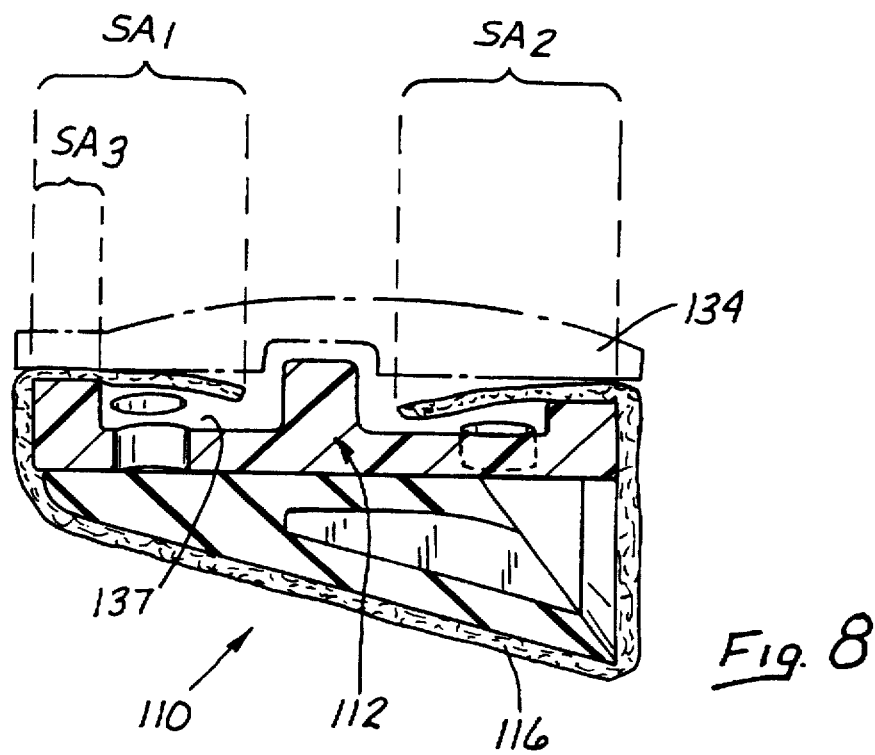
FIG. 8 is a schematic diagram illustrating the preferred sizing of the friction-mitigating protuberance(s) of the present invention in a rotatable prosthetic heart valve.

The detailed description set forth below in connection with the appended drawings is intended as a description of the presently preferred embodiments of the invention, and is not intended to represent the only forms in which the present invention may be constructed or utilized. The description sets forth the functions and the sequence of steps for constructing and operating the invention in connection with the illustrated embodiments. It is to be understood, however, that the same or equivalent functions may be accomplished by different embodiments that are also intended to be encompassed within the spirit and scope of the invention.

Suture rings for rotatable prosthetic heart valves of the present invention are illustrated in FIGS. 1–8. These figures include showings of two (2) presently preferred embodiments of the invention—one for aortic valve replacement and the other for mitral valve replacement. However, such figures and the accompanying description is by way of example only and not by way of limitation. Those skilled in the art will appreciate that the sewing ring of the present invention may be utilized in various other applications.

In general, the present invention provides prosthetic heart valves which comprise an annular valve body having at least one occluder member (e.g., a pair of pivoting leaflets) positioned therewithin. A rotatable suture ring 10, 110 is mounted about the outer surface of the annular valve body 34, 134. Such suture ring 10, 110 comprises a ring member 12, 112 having an annular sponge 14, 114 disposed thereabout, and a fabric material 16, 116 covering. The fabric material 16, 116 may comprise a knitted or woven material with or without a velour structure, from polytetraflouroethylene, polypropylene or polyester. The fabric material 16, 116 is preferably formed as a seamless tube. The fabric material 16, 116 extends into the region between the ring member 12, 112 and the outer surface of the annular heart valve body 34, 134. At least one friction-mitigating protuberance, such as an annular rib 36, 136 which serves to decrease the friction-creating surface area which exerts pressure upon the portion of the fabric material 16, 116 which is captured between the heart valve body 34, 134 and the ring member 12, 112. In this manner, such protuberance, such as an annular rib 36, 136, serves to control and limit the frictional resistance to rotation of the suture ring 10, 110 despite normal variations in the thickness of the fabric material 16, 116.

It will be appreciated that, as an alternative to forming the protuberance, such as an annular rib 36, 136 on the ring member 12, 112, such protuberances, such as annular rib(s) may alternatively be formed on the outer surface of the heart valve body 34, 134 to thereby produce the same friction-mitigating effect.

Description of The Suture Ring For a Rotatable Mitral Valve

Referring now to FIGS. 1–3a, the first embodiment of the present invention generally comprises a suture ring 10 configured for use with an artificial mitral valve. The suture ring 10 generally comprises a ring member 12 to which an annular sponge 14, formed of silicone rubber or other material, is attachable. A fabric material 16 generally covers the ring member 12 and the annular sponge 14, as discussed in detail below.

Accordingly to the first preferred embodiment of the present invention, the ring member 12 comprises an outer surface 18, an inner surface 20, a proximal edge 22, and a distal edge 24. A plurality of apertures 26 extend through the ring member 12, (i.e., from the outer surface 18 to the inner surface 20 thereof), so as to facilitate sewing of the fabric material 16 thereto.

The ring member 12, further comprises an annular tracking rib 28 which is configured to be received within a generally complimentary annular tracking groove 30 formed in an outer surface 32 of the annular valve body 34.

Figure 6:
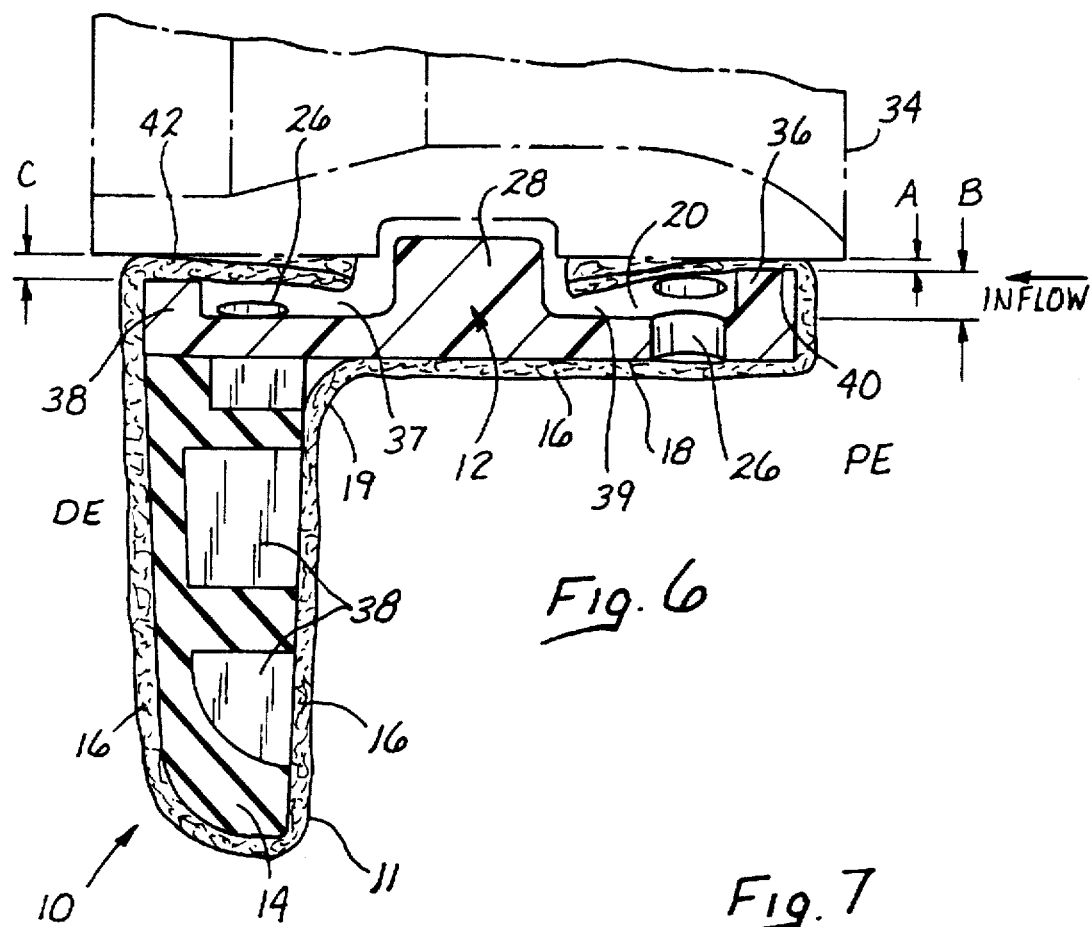
FIG. 6 is a cross sectional view of the suture ring of FIG. 1.

The ring member 12, further comprises at least one, preferably two protuberances, formed upon the inner surface 20 of the ring member 12 so as to mitigate the frictional resistance to rotation which results from compression of the fabric material 16 which is interposed between the inner surface 20 of the ring member 12 and the outer surface 32 of the annular valve body 34, as best shown in FIG. 6 and described in detail below. The protuberances preferably define first 36 and second 38 annular ribs, preferably formed adjacent the distal 24 and proximal 22 edges of the ring member 12, respectively.

As used herein, the term proximal refers to that end or edge of the device which is on the upstream blood flow side thereof and the term distal refers to that end or edge of the device which is on the downstream blood flow side of the device. The proximal end of the device is indicated in the drawings by the letters PE and the distal end of the device is indicated in the drawings by the letters DE.

Alternatively, the such protuberances may be formed upon the annular valve body 34, so as to achieve a like effect, wherein the frictional resistance to rotation due to compression of the fabric material between the inner surface 20 of the ring member 12 and the outer surface 32 of the annular valve body 34 is likewise substantially mitigated.

According to the preferred embodiment of the present invention, the ring member 12 is comprised of a polyacetal material, one example of which is DELRIN (a registered trademark of E. I. Du Pont De Nemours & Co., Inc., Wilmington, Del.). As those skilled in the art will appreciate, the ring member 12 may be comprised of various other polymer materials such as polyacetals, polyesters, ultra high molecular weight polyethylene, polysulfones, polyimides, polyether keytones (e.g., PEEKS), liquid crystalline polymers (e.g., LCPs), and/or carbon fiber composites. The ring member may alternatively be formed of a biocompatable metal or metal alloy, such as titanium, Elgiloy, or zirconium.

If formed of a polymer material, required tolerances for the ring (e.g., as an ellipse) member are reduced. Indeed, the ring member may formed, in an out-of-round condition, since attachment to a valve body will force the ring member to assume the desired annular shape.

According to the preferred embodiment of the present invention, the ring member 12 is generally rigid, such that a tool or fixture (FIG. 8) is typically required to effect installation of the suture ring 10 upon the annular valve body 34. Alternatively, the ring member 12 may be substantially flexible and use of the installation tool may be optional.

The annular sponge 14 is comprised of a biocompatable resilient material, preferably silicone rubber. Those skilled in the art will appreciate that various other needle penetrable materials, such as felt or a textile or polymer fabric filler, may likewise be suitable for use as the annular sponge 14. The needle-penetrable annular sponge 14 preferably comprises a plurality of cells 39 (best shown in FIG. 3a), which enhance the resiliency thereof, so as to facilitate desired deformation of the flange or outer periphery 11 (FIG. 1) of the suture ring 10, thereby allowing it to conform to the natural mitral root, so as to maximize the orifice to annulus ratio. The cells 39 also make the suture ring 10 more easily penetrable by a needle and mitigate dulling of the needle, as would occur if a solid annular member were utilized instead of a sponge.

The needle-penetrable fabric material 16 preferably comprises a biocompatible woven or knitted material, such as polyester or other suitable material. The fabric may be treated or coated with various chemical materials/coatings to improve biocompatability (e.g., heparin, chemicallybound heparin, carbon coatings, etc.).

Depending on the manufacturing or weaving methods used, and variations in the source of supply from which the material is obtained, the needle-penetrable fabric material may be subject to some variations in thickness. For example, the typical woven polyester material used for this application varies from approximately 0.008 inch to approximately 0.014 inch in thickness. In view of this typical variation in the thickness of the needle-penetrable fabric material 16, the friction mitigating protuberances of the present invention, such as the first 36 and second 38 annular ribs, will be sized relative to the thickness of the fabric material interposed therebetween, so as to permit routine rotation of the suture ring 10 relative to the annular valve body 34 over the entire range of fabric thicknesses wherein the needle-penetrable fabric material 16 is expected to vary.

Referring now to FIG. 6, the fabric material 16 is preferably sewed to the ring member 12 at both the distal and proximal end thereof. The fabric material 16 is sewn to the ring member 12 at the distal end thereof by repeatedly passing a biocompatable thread through apertures 26 so as to sew the fabric material to both the outer surface 18 and the inner surface 20 of the ring member 12.

In a similar fashion, the fabric material 16 is sewed to the proximal end of the ring member 12 by repeatedly passing biocompatible thread through apertures 26 at the proximal end of the ring member 16. This is preferably accomplished by passing the thread through the fabric material 16 on the outer surface 18 of the ring member 12 at the corner 19 formed by the annular sponge 14 and the ring member 12. Such sewing of the fabric material 16 to the ring member 12 assures that the fabric material 16 is pulled tightly into the corner 19 and also held tightly along the surfaces of the annular sponge 14 and the ring member 12.

Operation of The Rotatable Suture Ring Mounted on a Prosthetic Mitral Valve

Referring now to FIG. 6, operation of the suture ring for a rotatable artificial mitral valve is illustrated. According to the preferred embodiment of the present invention, a torque control gap 40, having a width of dimension A, is defined by the first annular rib 36 at the proximal or inflow end PE of the valve. In a similar fashion, a second gap 42, dimension C, is formed at the distal or outflow end DE of the valve.

The torque control gap 40 is configured to have a gap width, dimension A, which compresses the fabric material 16 captured between the first annular rib 36 and the annular valve body 34 sufficiently to provide a desired degree of frictional resistance to rotation. Thus, the ease with which the annular valve body 34 is rotatable within the suture ring 10 is substantially determined by the width, dimension A, of the torque control gap 40.

As those skilled in the art will appreciate, frictional resistance to rotation of the annular valve body 34 within the suture ring 10 must be sufficient to prevent undesirable or inadvertent rotation thereof after the annular valve body 34 has been rotated to a desired orientation by the physician. Thus, once the annular valve body 34 has been oriented as desired, the frictional resistance to rotation must be sufficient to maintain the annular valve body 34 at the desired rotational orientation thereof. As such, a minimum frictional resistance to rotation is defined.

As discussed in detail above, the frictional resistance to rotation must be less than that amount which would require excessive force by the surgeon and/or which could result in damage to the annular valve body 34, suture ring 10, and/or the patient. Thus, a maximum frictional resistance to rotation is definable for each particular design and type of valve.

By sizing the torque control gap 40 such that its width corresponds to a given thickness of fabric material 11, a desired compression of the fabric material 11 is provided and the frictional resistance to rotation is maintained within the desired range. In this manner, the width, dimension A, which corresponds to the normal range of thickness and coefficient of friction of the fabric material 16, such that sufficient frictional drag will be produced to prevent inadvertent rotation of the suture ring 10 on the valve body 34.

The second gap 42 defined by the annular rib 38 on the proximal end of the suture ring 10 is sized so as to provide minimal frictional resistance to rotation for a given thickness of fabric material 16. The gap 42, defined by dimension C, is however sufficiently small to substantially prevent leakage of blood into the second void 37 formed intermediate the ring member 12 and the annular valve body 34. In a similar fashion, substantial blood leakage into the first void 39 formed intermediate the ring member 12 and the annular valve body 34 is prevented by the compression of the fabric material 16 within the narrower torque control gap 40.

Thus, the first or torque control gap 40 is preferably smaller than the second gap 42, such that the contribution to the frictional resistance to rotation from the second gap 42 is substantially less than that from the first gap 40.

Thus, according to the present invention, compression of the fabric material 16 between the ring member 12 of the suture ring 10 and the annular valve 34 is both substantially minimized and controlled. Compression of the fabric material 16 is substantially minimized since only a portion of the fabric material 16 interposed between the ring member 12 and the annular valve 34 is compressed. Most of the fabric material 16 interposed between the ring member 12 and the annular valve body 34 is disposed within the first 39 and second 37 voids, both having a width, dimension B, which is substantially greater than dimensions A and C, such that the fabric material within the voids 37, 39 is not substantially compressed. As discussed in detail above, compression of a portion of the fabric material 16 is controlled by matching the torque control gap 40, dimension A, to the thickness of the fabric material 16.

Thus, according to the present invention, after the suture ring 10 has been sewn in place upon the endogenous valve annulus of the patient-host, then the valve is rotated, preferably using a tool, so as to prevent damage to the occluder leaflets thereof, to a desired position. By controlling the resistance of the rotation of the valve body 34 within the suture ring 10, it is assured that the valve can be so rotated without the application of excessive torque thereto. Thus, the potential for damage to the suture ring, valve, and/or endogenous tissue is mitigated.

After the valve has been rotated to the desired orientation thereof, the frictional resistance to rotation is sufficient to maintain the valve in the desired position.

Description of the Suture Ring For a Rotatable Aortic Valve

Referring now to FIGS. 4 and 5, the second embodiment of the present invention generally comprises a suture ring 110 configured for use with an artificial aortic valve. As in the mitral valve discussed above, the suture ring 110 generally comprises a ring member 112 to which an annular sponge 114 is attached. A fabric material 116 generally covers the ring member 112 and the annular sponge 114.

As in the first embodiment of the present invention, the ring member 112 comprises an outer surface 118, an inner surface 120, a proximal edge 122, and a distal edge 124. A plurality of apertures 126 extend throughout the ring member 112.

The ring member 112 of the second embodiment thereof further comprises an annular tracking rib 128 which is configured to be received within a generally complimentary annular tracking groove 130 formed in the outer surface of the annular valve body 134 of the aortic valve. The ring member 112 further comprises first 136 and second 138 annular ribs, preferably formed adjacent the distal 124 and proximal 122 edges of the ring member 112, respectively.

Thus, the suture ring 110 of the second embodiment of the present invention is generally similar to that of the first embodiment thereof. One important exception is that the configuration of the sponge member 114 is generally conical in shape, thus defining a substantially constant taper from the proximal end to the distal end thereof, such that the distal end has a substantially greater diameter than the proximal end of the sponge member 114. Additionally, the valve body 134 of the aortic valve, as well as the sewing ring 110 therefor, are of slightly less diameter than in the mitral valve.

The sponge member 114 preferably comprises open cells 115, which contribute to the resiliency thereof, and also facilitate sewing therethrough, as discussed regarding the first embodiment of the present invention.

The fabric material 116 is preferably sewed to the ring member 112 are repeatedly passing biocompatible thread through the apertures 126 on the distal end of the ring 10 member 112 and then repeating the process for the proximal end thereof. During such sewing, the thread passes through the annular sponge 114 on both the distal and proximal ends of the ring member 112.

The ring member 112 preferably comprises an annular tracking rib 128 which was received within a generally complimentary annular tracking groove 130 formed upon the annular body 134 of the aortic valve.

Operation of the Rotatable Suture Ring Mounted on a Prosthetic Aortic Valve

Figure 7:
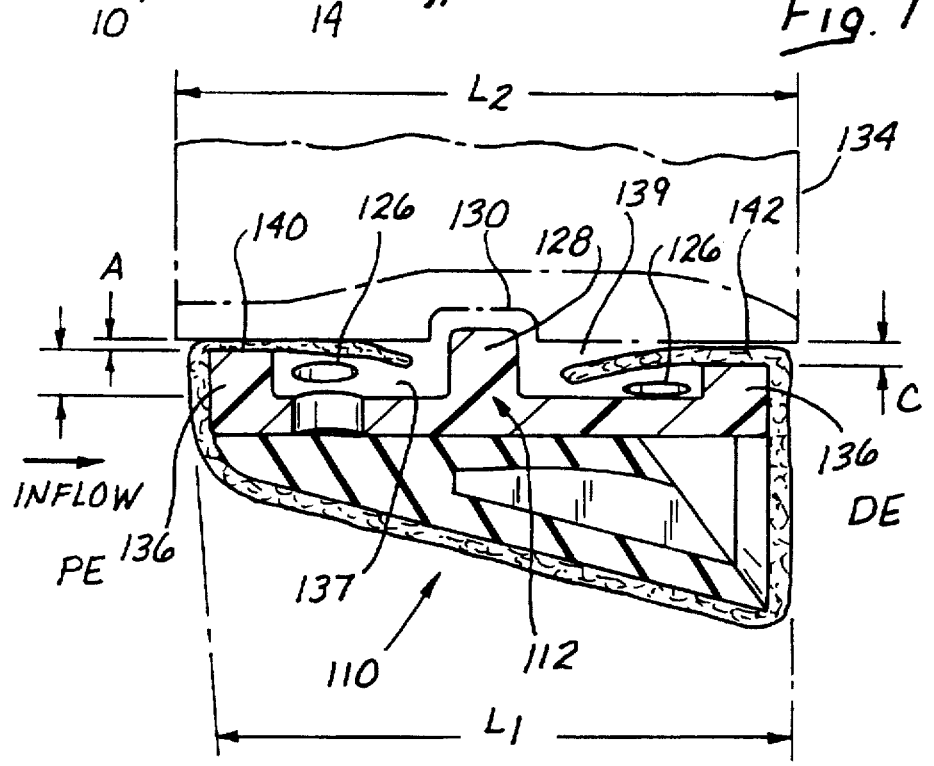
FIG. 7 is a cross section view of the suture ring of FIG. 4.
Figure 9:
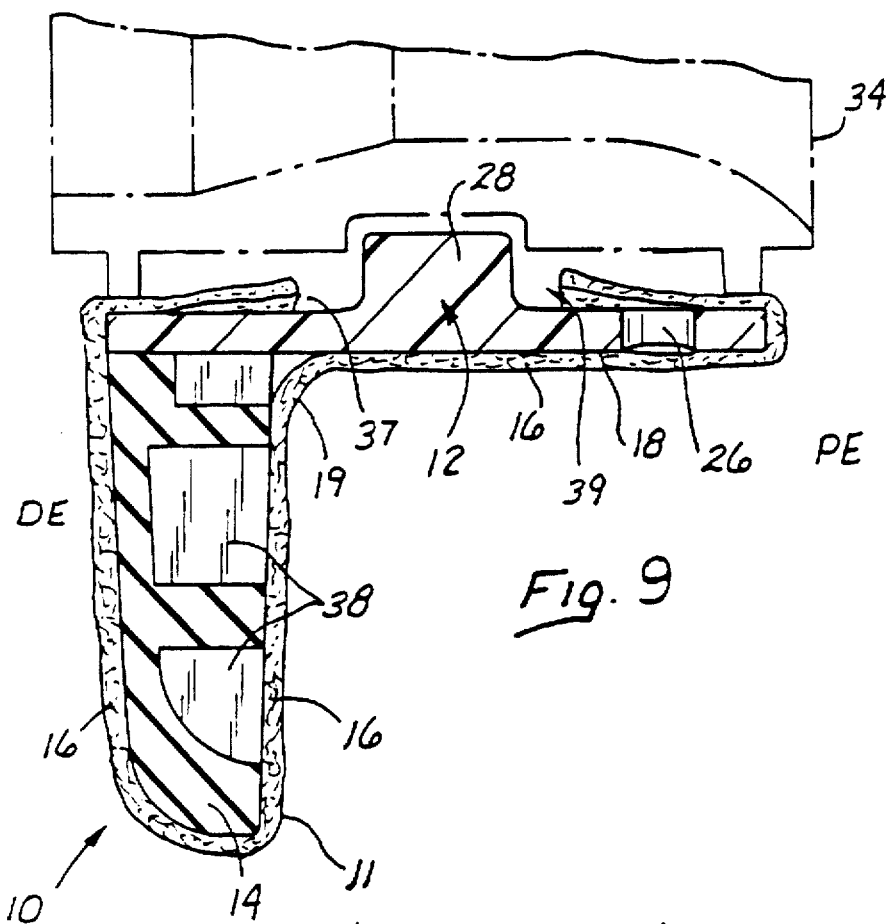
FIG. 9 is a cross-sectional diagram of another embodiment where there are protuberances on the valve body.
Figure 10:
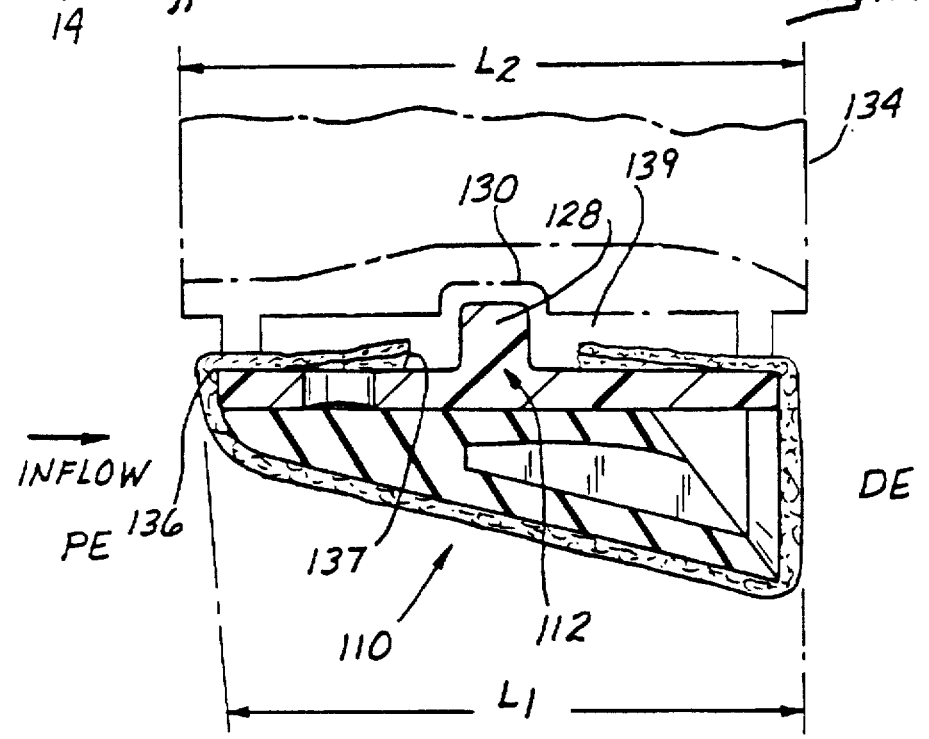
FIG. 10 is a cross-sectional diagram of another embodiment where there are protuberances on the valve body.

Referring now to FIG. 7, operation of the suture ring 110 for a rotatable artificial aortic valve is illustrated. According to the preferred embodiment of the present invention, the torque control gap 140, having a width of dimension A, is defined by the first annular rib 136 at the proximal end of the suture ring 110. In a similar fashion, a second gap 142, dimension C, is formed at the proximal end of the suture ring 110.

The relative sizing (width) and functions of the torque control gap 140 and the second gap 142 are the same as described hereabove with respect to the first embodiment of the present invention.

Assembly of the Rotatable Heart Valves of the Present Invention

The suture ring 10, 110 may be mounted upon the heart valve body 34, 134 by any suitable means. Preferably, the rigid ring member 12, 112 is formed of material which may be elastically expanded to a sufficient degree to permit the suture ring 10, 110 to be snap-fit onto the valve body 34, 134 such that the tracking rib 28, 128 of the suture ring 10, 110 becomes positioned within the tracking groove 30, 130 of the heart valve body 34, 134.

Such expansion of the rigid ring member 12, 112 may be accomplished by inserting outwardly moveable projections or "fingers" within the assembled sutured ring 10, 110 as it is being snap-fit onto the heart valve body 34, 134. Alternatively, a tapered, frusto conical dilator may be utilized to dilate the rigid ring member 12, 120 of the suture ring 10, 100 as the suture ring 10, 100 as the suture ring 10, 100 is being snap fit onto the heart valve body 34, 134.

Preferred Sizing of the Suture Ring For Minimally Invasive Surgical Implantation Various minimally invasive surgical procedures are presently being developed to permit surgical valve replacement in a human heart through minimal access incisions, typically no more than 0.5–1 inch in length. Typically, these minimally invasive surgical techniques employ the use of one or more thorascopes to permit the surgeon to visualize the interior of the thoracic cavity, and the concomitant deployment of one or more endoscopic surgical instruments (e.g., thoracoscopes) into the thoracic cavity through minimal access incisions formed at desired locations about the thorax of the patient.

In light of these recently-developed minimally invasive surgical techniques, it is desirable that at least some of the embodiments of the present invention be constructed in a manner which minimizes the size of the prosthetic valve in at least one dimension, thereby facilitating passage of the valve into the thoracic cavity and into its intended intracardiac implantation site, through relatively small minimal access incisions or openings.

In this regard, it is desirable that the longitudinal length L of the aortic or mitral sewing ring 10, 110 be no greater than the longitudinal length $L_2$ of the valve body.

By minimizing the length of the suture ring 10, 110 such that it does not protrude beyond the longitudinal ends of the valve body 34, 134, the longitudinal length of the prosthetic valve/suture ring assembly is minimized.

It is understood that the examples and embodiments described herein and shown in the drawings represent only the presently preferred embodiments of the invention, and are not intended to exhaustively describe in detail all possible embodiments in which the invention may take physical form. Indeed, various modifications and additions may be made to such embodiments without departing from the spirit and scope of the invention. For example, various different cross sectional configurations of the sewing ring are contemplated. As those skilled in the art will appreciate, the annular sponge thereof may be configured so as to facilitate attachment to various modified configurations of the endogenous valve annulus. Further, various different configurations of the annular tracking rib of the sewing ring member and/or the annular tracking groove of the valve body may likewise be suitable.

What is claimed is:

1. A rotatable artificial heart valve apparatus comprising:
   a) an annular valve body having a blood flow passage extending longitudinally therethrough and an outer surface;
   b) at least one occluder mounted within the blood flow passageway of said annular valve body to intermittently block the flow of blood through said passageway;
   c) a suture ring mounted on the outer surface of said valve body and rotatable thereon, said suture ring comprising:
      i) a ring member having an inner surface, an outer surface, a proximal edge, and a distal edge; and,
      ii) a needle-penetrable fabric covering disposed on said ring member, a portion of said fabric being interposed between the inner surface of said ring member and the outer surface of said valve body;
   d) at least one protuberance formed on the inner surface of said ring member defining the only surface on said valve body which compresses said portion of said fabric between the inner surface of said ring member and said outer surface of the valve body.

2. The heart valve apparatus of claim 1 wherein said at least one protuberance comprises:
   a) a first annular rib formed about the inner surface of said ring member adjacent the proximal edge thereof; and,
   b) a second annular rib member formed about the inner surface of said ring member adjacent the distal edge thereof.

3. The heart valve apparatus of claim 1 wherein:
   a) an annular tracking groove is formed in the outer surface of said heart valve body;
   b) an annular tracking rib is formed on the inner surface of said ring member; and,
   c) the annular tracking rib formed on the inner surface of said ring member being sized and configured to snap into the annular tracking groove formed on the outer surface of said valve body so as to retain said ring member on said valve body such that said valve body is rotatable relative to said suture ring.

4. The heart valve apparatus of claim 1 wherein said needle-penetrable fabric cover is formed of fabric material selected from the list of materials consisting of:
   polytetrafluoroethylene;
   polypropylene;
   polyester; and,
   velour.

5. The heart valve apparatus of claim 1 wherein said needle-penetrable fabric is woven.

6. Then heart valve apparatus of claim 1 wherein said needle-penetrable fabric material is knitted.

7. The heart valve apparatus of claim 1 wherein the entire surface of said heart valve body and said ring member between which said fabric material is interposed is definable as a first surface area, and wherein the friction-creating contact surfaces of the protuberance(s) and adjacent portion of the heart valve body is definable as a second surface area, and wherein said second surface area is no more than 20% of said first surface area.

8. The heart valve apparatus of claim 1 wherein said heart valve apparatus is intended for implantation at the mitral location, and wherein said suture ring further comprises an annular sponge positioned about the outer surface of said ring member, adjacent the distal end thereof, said sponge being covered by said needle-penetrable fabric material, and being configured so as to define a flange having an outer diameter substantially greater than the outer diameter of the ring member.

9. The heart valve apparatus of claim 1 wherein said heart valve apparatus is intended for implantation at the aortic location, and wherein said suture ring further comprises an annular sponge positioned about the outer surface of said ring member, said annular sponge extending generally from the proximal edge of the ring member to the distal edge thereof and being tapered so as to define a smaller outer diameter at the proximal edge of the ring member than at the distal edge thereof.

10. The heart valve apparatus as recited in claim 2 further comprising a friction control gap defined by one of said first and second annular ribs and said annular valve body, a width of said friction control gap cooperating with a thickness of said fabric material to determine torque required to effect rotation of the valve body within the suture ring.

11. The heart valve apparatus of claim 1 wherein the length of said suture ring is no greater than the length of said valve body, thereby facilitating passage of the apparatus through a minimal access incision.

12. A rotatable artificial heart valve apparatus comprising:
   a) an annular valve body having a blood flow passageway extending longitudinally therethrough and an outer generally cylindrical surface having a nominal diameter and a groove therein having a diameter less than the nominal diameter;

b) at least one occluder mounted within the blood flow passageway of said annular valve body to intermittently block the flow of blood through said passageway;

c) a suture ring mounted on the outer surface of said valve body and rotatable thereon, said suture ring comprising:

i) a ring member having an inner surface, an outer surface, a proximal edge, and a distal edge; and, ii) a needle-penetrable fabric covering disposed on said ring member, a portion of said fabric being interposed between the inner surface of said ring member and the outer surface of said valve body;

d) at least one protuberance formed on the outer surface of said valve body projecting outward from the outer surface and defining the only surface on said valve body which compresses said portion of said fabric between the inner surface of said ring member and said outer surface of the valve body.

13. The heart valve apparatus of claim 12 wherein said at least one protuberance comprises:

a) a first annular rib formed about the inner surface of said valve body adjacent the proximal edge thereof; and, b) a second annular rib member formed about the inner surface of said valve body adjacent the distal edge thereof.

14. The heart valve apparatus of claim 12 further comprising an annular tracking rib formed on the inner surface of said ring member the annular tracking rib formed on the inner surface of said ring member being sized and configured to snap into the groove formed on the outer surface of said valve body so as to retain said ring member on said valve body such that said valve body is rotatable relative to said suture ring.

15. The heart valve apparatus of claim 12 wherein said needle-penetrable fabric cover is formed of fabric material selected from the list of materials consisting of:
polytetrafluoroethylene;
polypropylene;
polyester; and
velour.

16. The heart valve apparatus of claim 12 wherein said needle-penetrable fabric is woven.

17. The heart valve apparatus of claim 16 wherein said needle-penetrable fabric is woven velour.

18. Then heart valve apparatus of claim 12 wherein said needle-penetrable fabric material is knitted.

19. The heart valve apparatus of claim 18 wherein said needle-penetrable fabric material is knitted velour.

20. The heart valve apparatus of claim 12 wherein said needle-penetrable fabric material comprises a seamless tube.

21. The heart valve apparatus of claim 12 wherein the entire surface of said heart valve body and said ring member between which said fabric material is interposed is definable as a first surface area, and wherein the friction-creating contact surfaces of the protuberance(s) and adjacent portion of the heart valve body is definable as a second surface area, and wherein said second surface area is no more than 20% of said first surface area.

22. The heart valve apparatus of claim 12 wherein said heart valve apparatus is intended for implantation at the mitral location, and wherein said suture ring further comprises an annular sponge positioned about the outer surface of said ring member, adjacent the distal end thereof, said sponge being covered by said needle-penetrable fabric material, and being configured so as to define a flange having an outer diameter substantially greater than the outer diameter of the ring member.

23. The heart valve apparatus of claim 12 wherein said heart valve apparatus is intended for implantation at the aortic location, and wherein said suture ring further comprises an annular sponge positioned about the outer surface of said ring member, said annular sponge extending generally from the proximal edge of the ring member to the distal edge thereof and being tapered so as to define a smaller outer diameter at the proximal edge of the ring member than at the distal edge thereof.

24. The heart valve apparatus as recited in claim 13 further comprising a friction control gap defined by one of said first and second annular ribs and said annular valve body, a width of said friction control gap cooperating with a thickness of said fabric material to determine torque required to effect rotation of the valve body within the suture ring.

25. The heart valve apparatus of claim 12 wherein the length of said suture ring is no greater than the length of said valve body, thereby facilitating passage of the apparatus through a minimal access incision.

26. A suture ring which is adapted to be rotatably mountable on the generally cylindrical outer surface of a prosthetic heart valve apparatus, said suture ring comprising:

a) a ring member having an inner surface, an outer surface, a proximal edge, and a distal edge;

b) a needle-penetrable fabric covering disposed on said ring member, a portion of said fabric being interposed between the ring member and the outer surface of the prosthetic heart valve apparatus, when the suture ring is mounted on said prosthetic heart valve apparatus; and c) at least one protuberance formed on said inner surface of said ring member defining the only surface on said suture ring which compresses said portion of said fabric between the inner surface of said ring member and the outer surface of the prosthetic heart valve apparatus, when the suture ring is mounted on said prosthetic heart valve apparatus.

27. The suture ring of claim 26 wherein said at least one protuberance comprises:

a) a first annular rib formed about the inner surface of said ring member adjacent the proximal edge thereof; and, b) a second annular rib member formed about the inner surface of said ring member adjacent the distal edge thereof.

28. The suture ring of claim 26 wherein the suture ring is intended for mounting on a prosthetic heart valve apparatus which has an annular tracking groove formed about it's generally cylindrical outer surface, and wherein said suture ring further comprises:

an annular tracking rib formed on the inner surface of said ring member, said annular tracking rib being sized and configured to snap into the annular tracking groove formed on the outer surface of the prosthetic heart valve apparatus so as to retain said ring member on said heart valve apparatus, such that said heart valve apparatus is rotatable relative to said suture ring.

29. The suture ring of claim 26 wherein said needle-penetrable fabric covering is formed from material selected from the group consisting of:
polytetrafluoroethylene;
polypropylene;
polyester; and, velour.

30. The suture ring of claim 26 wherein said needle-penetrable fabric is woven.

31. The suture ring of claim 26 wherein said needle-penetrable fabric is knitted.

32. The heart valve apparatus of claim 26 wherein the entire surface of said heart valve body and said ring member between which said fabric material is interposed is definable as a first surface area, and wherein the friction-creating contact surfaces of the protuberance(s) and adjacent portion of the heart valve body is definable as a second surface area, and wherein said second surface area is no more than 20% of said first surface area.

33. The suture ring of claim 26 wherein said suture ring is configured for use with a heart valve apparatus which is intended for implantation at the mitral location, and wherein said suture ring further comprises an annular sponge positioned about the outer surface of said ring member, adjacent the distal end thereof, said sponge being covered by said needle-penetrable fabric material, and being configured so as to define a flange having an outer diameter substantially greater than the outer diameter of the ring member.

34. The suture ring of claim 26 wherein said suture ring is configured for use with a heart valve apparatus intended for implantation at the aortic location, and wherein said suture ring further comprises an annular sponge positioned about the outer surface of said ring member said annular sponge extending generally from the proximal edge of the ring member to the distal edge thereof and being tapered so as to define a smaller outer diameter at the proximal edge of the ring member than at the distal edge thereof.

35. The heart valve apparatus of claim 1 wherein said needle-penetrable fabric cover is a seamless tube.

36. A rotatable artificial heart valve apparatus comprising:
   a) an annular valve body having a blood flow passageway extending longitudinally therethrough and an outer surface;
   b) a suture ring mounted on the outer surface of said valve body and rotatable thereon, said suture ring including an inner surface, an outer surface, a proximal edge, and a distal edge;
   c) a fabric sheet being interposed between the inner surface of said suture ring and the outer surface of said valve; and
   d) at least one protuberance formed on either the outer surface of said valve body or the inner surface of said suture ring for compressing said fabric sheet between the inner surface of said suture ring and said outer surface of the valve body, said at least one protuberance defining a surface area of no more than 20% of the smaller of the surface areas of the inner surface of the suture ring and the outer surface of the valve body, wherein the at least one protuberance defines the only surface on said suture ring which compresses said fabric sheet between the inner surface of said suture ring and the outer surface of said valve body.

37. The rotatable artificial heart valve of claim 36, wherein there are two protuberances.

38. The rotatable artificial heart valve of claim 37, wherein the two protuberances are of differing heights.

39. The rotatable artificial heart valve of claim 37, wherein the valve body has inflow and outflow edges, and the protuberances are adjacent opposite edges.

40. The rotatable artificial heart valve of claim 36, wherein the valve body has an inflow and an outflow end, and the protuberance is adjacent one of the edges.

* * * * *